United States Patent [19]
Hamilton et al.

[11] Patent Number: 5,968,633
[45] Date of Patent: Oct. 19, 1999

[54] SELECTIVELY-ACTIVATIBLE SHEET MATERIAL FOR DISPENSING AND DISPERSING A SUBSTANCE ONTO A TARGET SURFACE

[75] Inventors: Peter Worthington Hamilton, Cincinnati; Kenneth Stephen McGuire, Wyoming; Richard Tweddell, III; Geneva Gail Otten, both of Cincinnati, all of Ohio

[73] Assignee: The Procter & Gamble Company, Cincinnati, Ohio

[21] Appl. No.: 08/869,602

[22] Filed: Jun. 6, 1997

[51] Int. Cl.⁶ .................. B32B 3/00; B32B 7/12
[52] U.S. Cl. ............ 428/174; 428/179; 428/187; 428/196; 428/200; 428/201; 428/343
[58] Field of Search .................... 428/174, 172, 428/156, 343, 42.1, 120, 179, 187, 196, 200, 201, 904.4

[56] References Cited

U.S. PATENT DOCUMENTS

| | | | |
|---|---|---|---|
| 2,338,749 | 1/1944 | Wilbur | 24/67 |
| 2,861,006 | 11/1958 | Salditt | 117/7 |
| 3,018,015 | 1/1962 | Agriss et al. | 217/53 |
| 3,312,005 | 4/1967 | McElroy | 40/2 |
| 3,386,846 | 6/1968 | Lones | 117/11 |
| 3,554,835 | 1/1971 | Morgan | 156/234 |
| 3,592,722 | 7/1971 | Morgan | 161/148 |
| 3,853,129 | 12/1974 | Kozak | 128/287 |
| 3,901,237 | 8/1975 | Cepuritis et al. | 128/284 |
| 3,937,221 | 2/1976 | Tritsch | 128/287 |

(List continued on next page.)

FOREIGN PATENT DOCUMENTS

| | | |
|---|---|---|
| 570960 | 12/1961 | Belgium . |
| 0 037 101 A1 | 10/1981 | European Pat. Off. ........ B65D 77/20 |
| 0 623 332 A1 | 9/1994 | European Pat. Off. ........ A61F 13/15 |
| 0 621 082 A1 | 10/1994 | European Pat. Off. .......... B05C 1/08 |
| 1 315 903 | 4/1963 | France . |
| 1429312 | 2/1966 | France . |
| 3-002292 | 1/1991 | Japan ................. A61F 13/56 |
| 07246216 | 9/1995 | Japan ................. A61F 13/56 |
| 975783 | 11/1964 | United Kingdom . |
| 1069445 | 5/1967 | United Kingdom . |
| WO 92/00187 | 1/1992 | WIPO ............... B32B 3/00 |
| WO 95/11945 | 5/1995 | WIPO ................ C09J 7/02 |
| WO 95/31225 | 11/1995 | WIPO ............. A61L 15/58 |
| WO 96/19173 | 6/1996 | WIPO ............. A61F 13/46 |
| WO 96/41604 | 12/1996 | WIPO ............. A61F 13/58 |
| WO 97/18276 | 5/1997 | WIPO ................ C09J 7/02 |

*Primary Examiner*—Donald Loney
*Attorney, Agent, or Firm*—William Scott Andes

[57] ABSTRACT

The present invention provides a selectively-activatible sheet material for dispensing and dispersing a substance onto a target surface. The sheet material comprises a three-dimensional sheet of material having a first side and a second side. The said first side has a plurality of hollow protrusions extending outwardly therefrom and separated from one another by valleys, while the second side has a plurality of depressions corresponding with the hollow protrusions. A substance adheres to and partially fills a location protected from external contact comprising the valleys and/or the depressions. The sheet material may be selectively activated by deforming the hollow protrusions to deliver the substance to a target surface, the substance having an effective viscosity upon activation which permits the substance to be liberated from its protected location and dispensed onto the target surface. Suitable substances include cleansing agents, medicinal agents, emollients, lubricants, colorants, preservatives, protectants, condiments, adhesives, fragrances, anti-perspirants, deodorants, and combinations thereof. The present invention also includes such materials having two or more substances of diverse composition, and substances which undergo a decrease in effective viscosity upon activation (such as shear-thinning substances) are particularly preferred. Additional layers of porous material may also be employed on the opposite side of the substance from the sheet material such that the substance may be dispensed through the porous material. Porous materials may provide additional beneficial interaction with the substance, including enhanced distribution and dispersal.

20 Claims, 2 Drawing Sheets

U.S. PATENT DOCUMENTS

| | | | |
|---|---|---|---|
| 3,943,609 | 3/1976 | Egan, Jr. | 24/73 |
| 3,967,624 | 7/1976 | Milnamow | 128/287 |
| 4,023,570 | 5/1977 | Chinai et al. | 128/290 R |
| 4,054,697 | 10/1977 | Reed et al. | 428/40 |
| 4,061,820 | 12/1977 | Magid et al. | 428/311 |
| 4,067,337 | 1/1978 | Ness | 128/287 |
| 4,181,752 | 1/1980 | Martens et al. | 427/54.1 |
| 4,273,889 | 6/1981 | Yamazaki et al. | 525/109 |
| 4,303,485 | 12/1981 | Levens | 204/159.24 |
| 4,336,804 | 6/1982 | Roeder | 128/290 R |
| 4,337,772 | 7/1982 | Roeder | 128/290 R |
| 4,342,314 | 8/1982 | Radel et al. | 128/287 |
| 4,376,440 | 3/1983 | Whitehead et al. | 604/387 |
| 4,392,897 | 7/1983 | Herrington | 156/66 |
| 4,397,905 | 8/1983 | Dettmer et al. | 428/180 |
| 4,410,130 | 10/1983 | Herrington | 383/62 |
| 4,460,634 | 7/1984 | Hasegawa | 428/124 |
| 4,508,256 | 4/1985 | Radel et al. | 228/152 |
| 4,509,908 | 4/1985 | Mullane, Jr. | 425/290 |
| 4,514,345 | 4/1985 | Johnson et al. | 264/22 |
| 4,519,095 | 5/1985 | Clayton | 383/86 |
| 4,528,239 | 7/1985 | Trokhan | 428/247 |
| 4,556,595 | 12/1985 | Ochi | 428/143 |
| 4,576,850 | 3/1986 | Martens | 428/156 |
| 4,578,069 | 3/1986 | Whitehead et al. | 604/370 |
| 4,587,152 | 5/1986 | Gleichenhagen et al. | 428/195 |
| 4,655,761 | 4/1987 | Grube et al. | 604/389 |
| 4,695,422 | 9/1987 | Curro et al. | 264/504 |
| 4,699,622 | 10/1987 | Toussant et al. | 604/389 |
| 4,743,242 | 5/1988 | Grube et al. | 605/389 |
| 4,778,644 | 10/1988 | Curro et al. | 264/557 |
| 4,839,216 | 6/1989 | Curro et al. | 428/134 |
| 4,894,275 | 1/1990 | Pelzer | 428/166 |
| 4,946,527 | 8/1990 | Battrell | 156/60 |
| 4,959,265 | 9/1990 | Wood et al. | 428/343 |
| 5,008,139 | 4/1991 | Ochi et al. | 428/40 |
| 5,080,957 | 1/1992 | Leseman et al. | 428/167 |
| 5,098,522 | 3/1992 | Smurkoski et al. | 162/358 |
| 5,141,790 | 8/1992 | Calhoun et al. | 428/40 |
| 5,176,939 | 1/1993 | Shepherd | 427/146 |
| 5,221,276 | 6/1993 | Battrell | 604/389 |
| 5,245,025 | 9/1993 | Trokhan et al. | 536/56 |
| 5,246,762 | 9/1993 | Nakamura | 428/172 |
| 5,269,776 | 12/1993 | Lancaster et al. | 604/387 |
| 5,273,805 | 12/1993 | Calhoun et al. | 428/156 |
| 5,275,588 | 1/1994 | Matsumoto et al. | 604/372 |
| 5,296,277 | 3/1994 | Wilson et al. | 428/40 |
| 5,324,279 | 6/1994 | Lancaster et al. | 604/391 |
| 5,342,344 | 8/1994 | Lancaster et al. | 604/387 |
| 5,344,693 | 9/1994 | Sanders | 428/167 |
| 5,453,296 | 9/1995 | Lauritzen et al. | 427/208.6 |
| 5,458,938 | 10/1995 | Nygard et al. | 428/40 |
| 5,487,929 | 1/1996 | Rusincovitch, Jr. et al. | 428/40 |
| 5,514,122 | 5/1996 | Morris et al. | 604/387 |
| 5,518,801 | 5/1996 | Chappell et al. | 428/152 |
| 5,527,112 | 6/1996 | Dais et al. | 383/211 |
| 5,575,747 | 11/1996 | Dais et al. | 493/213 |
| 5,585,178 | 12/1996 | Calhoun et al. | 428/343 |
| 5,589,246 | 12/1996 | Calhoun et al. | 428/120 |
| 5,662,758 | 9/1997 | Hamilton et al. | 156/221 |

SELECTIVELY-ACTIVATIBLE SHEET MATERIAL FOR DISPENSING AND DISPERSING A SUBSTANCE ONTO A TARGET SURFACE

FIELD OF THE INVENTION

The present invention relates to a sheet-like materials containing a substance for application to a target surface. More particularly, the present invention relates to such materials wherein the substance may be released from the sheet material and distributed upon the target surface.

BACKGROUND OF THE INVENTION

In the art of dispensing, articles have been developed which are coated or impregnated with useful substances intended to be utilized when the article is contacted with a target surface. While there are advantages with having the substance present on or near the surface of such articles, there is often the drawback that the useful substance is unprotected and is subject to inadvertent contact before intended use. Inadvertent contact may lead to contamination of the substance, loss of the onto surfaces other than the desired target surface, and/or contamination of such other surfaces with the substance.

One approach to addressing such issues involves the use of protective packaging for the article, such as a sleeve, envelope, or other wrapping. While such protective packaging has proven effective in preserving the integrity and condition of the substance, depending upon the nature of the substance it is frequently the case that varying amounts of the substance remain on the article-facing surfaces of the packaging after it is removed from the article, thereby causing inefficient use of the substance. Moreover, such packaging adds additional non-value-added cost to the total price of the article. This approach also does not provide a method of control of uniformity of thickness of the substance since the product (substance) may be unevenly smeared on the carrier surface while in transit, storage, or upon opening of the sleeve, envelope, or other wrapping.

In the art of tapes, labels, and other articles using pressure sensitive adhesive to adhere an adhesive coated surface to a target surface, there has been recognized the problem of premature sticking to the target surface. That is, before the adhesive coated surface can be properly positioned over a target surface, inadvertent contact of the adhesive with the target surface causes premature sticking at one or more locations, thereby inhibiting proper positioning. Premature sticking may also cause contamination or degradation of the adhesive prior to final positioning upon the target surface.

One approach to addressing this problem involves the use of standoffs on a material surface, between which adhesive or adhesive elements are located. Standoffs include any means extending outwardly from an adhesive surface which is contacted first before the adhesive surface is exposed to contact by another surface. Such standoffs may be either deformable or may rely upon deformation of the target surface to provide contact between the adhesive and the target surface. Although approaches of this type have proven successful with adhesives, such materials are typically designed so that the adhesive remains attached to the material surface rather than transferring at least partially onto the target surface. Moreover, the adhesive typically remains substantially in its original placement relative to the target surface, such that a discontinuous or interrupted layer of adhesive fails to uniformly contact or coat the target surface.

Accordingly, it would be desirable to provide a sheet-like material which is capable of delivering and dispensing a substance onto a target surface for treating the target surface while the material is in contact with the target surface and/or leaving the substance on the target surface even after removal of the sheet material.

It would also be desirable to provide such a material which protects the substance from inadvertent contact prior to placement upon the desired target surface.

It would further be desirable to provide such a material which facilitates the dispersal of the substance on the target surface beyond the area of initial placement.

It would further be desirable to provide such a material which facilitates the dispersal of the substance on the target surface without user contact with the substance.

It would still further be desirable to provide such a material which may be readily and economically produced utilizing a continuous process.

SUMMARY OF THE INVENTION

The present invention provides a selectively-activatible sheet material for dispensing and dispersing a substance onto a target surface. The sheet material comprises a three-dimensional sheet of material having a first side and a second side. The said first side has a plurality of hollow protrusions extending outwardly therefrom and separated from one another by valleys, while the second side has a plurality of depressions corresponding with the hollow protrusions. A substance adheres to and partially fills a location protected from external contact comprising the valleys and/or the depressions. The sheet material may be selectively activated by deforming the hollow protrusions to deliver the substance to a target surface, the substance having an effective viscosity upon activation which permits the substance to be liberated from its protected location and dispensed onto the target surface. Suitable substances include cleansing agents, medicinal agents, emollients, lubricants, colorants, preservatives, protectants, condiments, adhesives, fragrances, anti-perspirants, deodorants, and combinations thereof.

The present invention also includes such materials having two or more substances of diverse composition, and substances which undergo a decrease in effective viscosity upon activation (such as shear-thinning substances) are particularly preferred. Additional layers of porous material may also be employed on the opposite side of the substance from the sheet material such that the substance may be dispensed through the porous material. Porous materials may provide additional beneficial interaction with the substance, including enhanced distribution and dispersal.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

As utilized herein, the term "selectively activatible" is used to refer to materials which exhibit substantially non-active properties when brought into contact with target surfaces until some action is taken by a user to "activate" the material to expose and dispense a substance. Accordingly, selectively-activatible properties differ from permanently-active strips of material which either maintain the substance in a permanently-deployed orientation or rely upon removal of liner materials (typically silicone-coated paper strips) or wrappings to expose the substance for use.

Selective activation of such materials allows the user to properly position opposing surfaces before activation is accomplished, as well as minimizing the likelihood of contamination of the substance. This characteristic permits the material to be manipulated in any desired mode without encountering the difficulties of premature contact of the substance with itself or to other portions of the sheet material or target surface without the need for separate release sheets, liners, spacers, or the like.

Although materials in accordance with the present invention may be provided with two active sides or surfaces, if desired for particular applications, in accordance with the present invention it is presently preferred to provide such material with only one active side and one inactive or inert side. Under some circumstances it may be acceptable or desirable to design the sheet material so as to form an intermittent or discontinuous layer of substance on its active surface, while in other circumstances the sheet material be designed so as to exhibit a continuous layer of substance on its active side. For some applications it may also be desirable to provide multiple products on a single side of the material, deposited in discrete discontinuous cells or regions (e.g., co-dispensing epoxies, catalyzed reactions, etc.).

Various means of activation are envisioned as being within the scope of the present invention, such as: mechanical activation by compression, mechanical activation by tensile forces, and thermal activation. However, it is envisioned that there may be or be developed other means of activation which would trigger an activation of the material which would be capable of functioning as herein described. In a preferred embodiment the active side is activatible by an externally applied force exerted upon the sheet of material. The force may be an externally applied compressive force exerted in a direction substantially normal to the sheet of material, an externally applied tensile force exerted in a direction substantially parallel to the sheet of material, or a combination thereof.

One such material of current interest for use in accordance with the present invention comprises a three-dimensional, conformable web comprising an active substance on at least one surface protected from external contact by the three-dimensional surface topography of the base material. After activation, such materials form a substance delivery system which delivers the substance to the target surface. Such materials comprise a polymeric or other sheet material which is embossed/debossed to form a pattern of raised "dimples" on at least one surface which serve as stand-offs to prevent a substance therebetween from contacting external surfaces until the stand-offs are deformed to render the structure more two-dimensional. Representative structures include those disclosed in commonly assigned, co-pending (allowed) U.S. patent application Ser. Nos. 08/584,638, filed Jan. 10, 1996 in the names of Hamilton and McGuire, entitled "Composite Material Releasably Sealable to a Target Surface When Pressed Thereagainst and Method of Making", 08/744,850, filed Nov. 8, 1996 in the names of Hamilton and McGuire entitled "Material Having A Substance Protected by Deformable Standoffs and Method of Making", 08/745,339, filed Nov. 8, 1996 in the names of McGuire, Tweddell, and Hamilton, entitled "Three-Dimensional, Nesting-Resistant Sheet Materials and Method and Apparatus for Making Same", 08/745,340, filed Nov. 8, 1996 in the names of Hamilton and McGuire, entitled "Improved Storage Wrap Materials". The disclosures of each of these applications are hereby incorporated herein by reference.

The three-dimensional structure comprises a piece of deformable material which has a first side formed to have a plurality of hollow protrusions separated by valleys. The plurality of hollow protrusions have outermost ends. The piece of material has a second side. The second side has a plurality of depressions therein corresponding to the plurality of hollow protrusions on the first side. The substance adheres to and partially fills the valleys between the plurality of hollow protrusions. In the limiting circumstance, the substance fills the valleys to a point at or slightly below the highest point of the protrusions, particularly if a meniscus is formed wherein the substance decreases in thickness with increasing distance from the surface of the protrusions. The substance has a surface below the outermost ends of the plurality of hollow protrusions, so that when a portion of the first side of the piece of deformable film is placed against a target surface, the plurality of hollow protrusions prevent contact between the substance and the target surface until the portion is deformed at the target surface. Preferably, the plurality of protrusions deform by modes which are selected from the group consisting of inverting, crushing, and elongating.

FIGS. 1–4 illustrate a preferred embodiment of a material according to the present invention, which comprises a three-dimensional sheet-like structure generally indicated as 10. Material 10 includes a deformed material 12 having hollow protrusions 14 and a layer of substance 16 located between protrusions 14. Protrusions 14 are preferably conical in shape with truncated or domed outermost ends 18. In the embodiment of FIGS. 1–4, protrusions 14 are equally spaced in an equilateral triangular pattern, all extending from the same side of the material. Preferably, the protrusions 14 have heights which are less than their diameters, so that when they deform, they deform by substantially inverting and/or crushing along an axis which is substantially perpendicular to a plane of the material. This protrusion shape and mode of deforming discourages protrusions 14 from folding over in a direction parallel to a plane of the material so that the protrusions cannot block substance between them from contact with a target surface.

Figure 1:
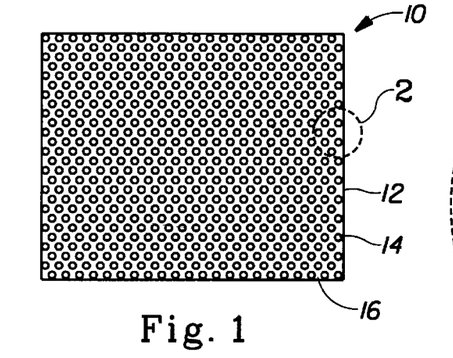
FIG. 1 is a top plan view of a preferred embodiment of the present invention, disclosing a piece of material having truncated conical protrusions surrounded by an interconnected pattern of substance.
Figure 2:
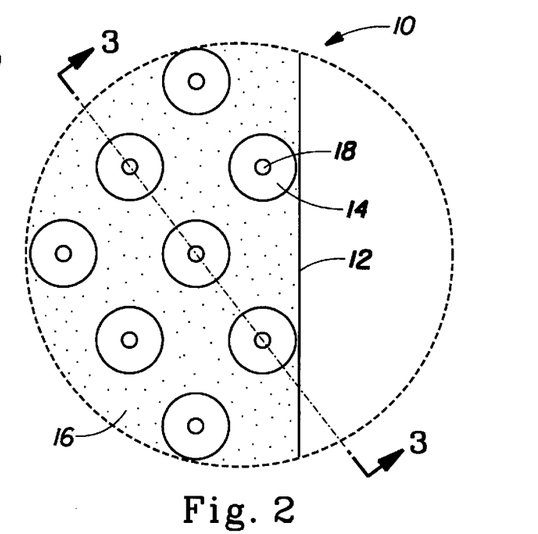
FIG. 2 is an enlarged partial top plan view of the material of FIG. 1, showing an array of protrusions.
Figures 3, 4:
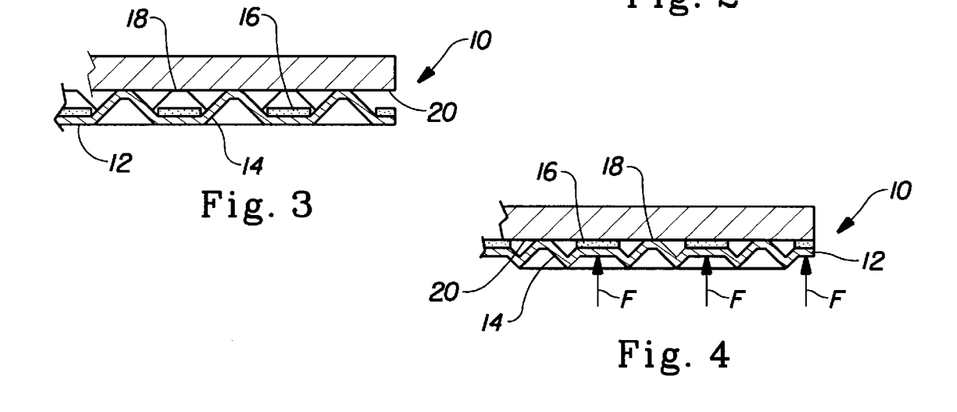
FIG. 3 is an elevational sectional view of the material of FIG. 2, taken along section line 3—3, showing the protrusions acting as standoffs for a substance layer between protrusions, such that a target surface contacting the outermost ends of the protrusions does not contact the substance layer.
FIG. 4 is an elevational sectional view similar to FIG. 3, showing the effect of pressing the material against the target surface, such that protrusions deform by substantially inverting and/or crushing to allow the substance layer between protrusions to contact the target surface.

FIG. 3 shows a target surface 20, which is smooth but which may have any surface topography, being spaced away from layer of substance 16 by outermost ends 18 of protrusions 14. Target surfaces in accordance with the present invention comprise any surface to which it is desired to apply the substance to be delivered. FIG. 4 shows target surface 20 contacting layer of substance 16 after protrusions 14 have been partially deformed under pressure applied to the non-substance side of material 12, as indicated by force F. The external target or contact surface may be either compliant or rigid and planar or non-planar. Having the three dimensional structure deform as described herein is preferred for use with a rigid target surface.

The more protrusions per unit area, the thinner the piece of material and protrusion walls can be in order to resist a given deformation force. The size and spacing of protrusions may be selected to provide a continuous substance path surrounding protrusions (as shown in the embodiment of FIGS. 1–4) so that a continuous pattern of the substance may be provided to a target surface, while also providing the optimum pattern of standoffs for selective activation.

Sheet materials utilized as a carrier material may be made from films comprising homogeneous resins or blends thereof. Single or multiple layers within the film structure are contemplated, whether co-extruded, extrusion-coated, laminated or combined by other known means. The key attribute of the sheet material is that it be formable to produce protrusions and valleys. Useful resins include polyethylene, polypropylene, PET, PVC, PVDC, latex structures, nylon, etc. Polyolefins are generally preferred due to their lower cost and ease of forming. Other suitable materials include aluminum foil, coated (waxed, etc.) and uncoated paper, coated and uncoated nonwovens, scrims, meshes, wovens, nonwovens, and perforated or porous films, and combinations thereof.

Different applications for the selectively-activatible sheet material will dictate the ideal size and density of protrusions, as well as the selection of the substances used therewith. It is believed that the protrusion size, shape and spacing, the web material properties such as flexural modulus, material stiffness, material thickness, hardness, deflection temperature as well as the forming process determine the strength of the protrusion. A "threshold" protrusion stiffness is required to prevent premature activation of the closure means due to the weight of overlaying layers of sheets or other forces, such as forces induced by shipping vibrations, mishandling, dropping and the like.

Inversion of protrusions minimizes protrusion spring back so that activation of the sheet material may be self-sustaining with little or no continuously-supplied forces. A resilient protrusion could be used, for example, where it is intended for the activation to be permanent, where aggressive adhesive overcomes spring back, or when the activation is intended to be momentary. Also, a resilient protrusion may be desirable where repeat use of the material is intended.

In the present invention, the term "substance" can mean a flowable substance which is substantially non-flowing prior to delivery to a target surface. "Substance" can also mean a material which doesn't flow at all, such as a fibrous or other interlocking material. "Substance" may mean a fluid or a solid. "Substance" is defined in this invention as any material capable of being held in open valleys and/or depressions of a three dimensional structure. Adhesives, electrostatics, mechanical interlocking, capillary attraction, surface adsorption, van der Waals forces, and friction, for example, may be used to hold the substances in the valleys and/or depressions. The substances are intended to be at least partially released therefrom when exposed to contact with external surfaces or when the three dimensional structure is deformed, heated, or otherwise activated. Of current interest in the present invention include substances such as gels, pastes, foams, powders, agglomerated particles, prills, microencapsulated liquids, waxes, suspensions, liquids, and combinations thereof.

The spaces in the three dimensional structure of the present invention are normally open; therefore it is desirable to have substances stay in place and not run out of the structure without an activation step. The activation step of the present invention is preferably deformation of the three dimensional structure by compression. However, an activation step to cause substance to flow could be heating the material to above room temperature or cooling it below room temperature. Or it could include providing forces excessive of the earth's gravity. It could also include other deforming forces, such as tensile forces and combinations of these activation phenomena.

The term "deformable material" is intended to include foils, polymer sheets, cloth, wovens or nonwovens, paper, cellulose fiber sheets, co-extrusions, laminates, and combinations thereof The properties of a selected deformable material can include, though are not restricted to, combinations or degrees of being: porous, non-porous, microporous, gas or liquid permeable, non-permeable, hydrophilic, hydrophobic, hydroscopic, oleophilic, oleophobic, high critical surface tension, low critical surface tension, surface pre-textured, elastically yieldable, plastically yieldable, electrically conductive, and electrically non-conductive.

The larger and more closely spaced the protrusions, the greater the likelihood of stretch occurring in a given material. Reducing the protrusion spacing to the closest possible spacing which is manufacturable may increase material stretch, but it may be beneficial in reducing the volume of substance between protrusions. Different applications for the formed material of the present invention will dictate ideal size and density of protrusions, as well as the selection of the substances used therewith.

In accordance with the present invention, the substance utilized in combination with the deformable material exhibits a selection of physical properties which enable it to be dispensed from its protected orientation within the three-dimensional structure and applied to the target surface. Such dispensation may be partial, or substantially or totally complete in nature.

To facilitate such dispensing, substance properties which are believed to be important include the relative affinity of the substance for the target surface versus that for the deformable material and the apparent viscosity or flowability of the substance after activation of the three-dimensional structure. It is presently believed that the substance should preferentially adhere to the target surface to a greater extent than to the deformable material and/or to a greater extent than for other portions of the substance itself. Said differently, the substance has a greater affinity for the target surface than for itself and/or for the deformable sheet material.

Substances may inherently possess viscosity and flow characteristics which permit their liberation from their protected location within the sheet material or may require viscosity modification to permit liberation and dispersal. Viscosity modification may be obtained by the selection of substances which undergo a change in viscosity in response to the mode of activation selected. For example, for a mechanical activation such as a compressive force it may be desirable, and preferably, to employ substances which are commonly referred to as "shear-thinning" (pseudoplastic) substances. Examples of such substances include polymer solutions, many gels and pastes such as dentrifice and body creams, paints, gelled wood stains, etc. Other materials behave as shear-thinning materials only after a certain threshold shear (yield stress) is reached or exceeded. Such materials are commonly referred to as Bingham plastic materials, and one common example of a substance exhibiting such behavior is the type of condiment known as ketchup.

Some of the factors believed to influence the adhesion or affinity of the substance for the target surface include: electrostatic or electrical charges; chemical bonds via hydrogen bonding, covalent bonding, ionic bonding, partial ionic bonds (partial dipolar attraction), van der Walls forces, osmotic forces, etc.; capillary pressure (suction); adsorption; absorption; vacuum/suction; etc. Other important factors include the wettability of the substance upon the target surface, as reflected by the contact angle of the substance on the target surface.

To facilitate spreading or dispersal of the substance upon the target surface, particularly to counteract the tendency of the substance to remain in a localized distribution pattern given the localized orientation upon the deformable substance, it is presently preferred to utilize substances which are tailored so as to be wettable on the target surface. Other factors which may aid in dispersion or distribution of the substance upon the target surface include the use of substances which exhibit a shear-thinning behavior, as well as mechanical spreading action provided by the user of the composite sheet material to impart a lateral mechanical motion after activation but prior to removal of the deformable material from the target surface. Such lateral mechanical action may also provide additional interaction with the substance such as for shear-thinning substances and may provide additional benefits such as lathering, foam generation, scrubbing/abrasive action, etc.

Successful dispersal occurs when a portion of the deposited or dispensed substance subsequently coats a portion of the target surface where the substance was not originally deposited. Upon removal of the sheet material from the target surface, at least some of the substance remains located on the target surface, preferably in a substantially-uniform fashion.

As discussed above, a wide variety of substances may be selected for use in accordance with the principles of the present invention. Representative substances for illustrative purposes include cleansing agents such as soaps and detergents, emollients such as lotions, medicinal agents such as ointments, anti-inflammatory creams, etc., health and beauty care products, including antiperspirants, deodorants, cosmetics, fragrances, and the like. Other more diverse applications for such a sheet material include applicators for automotive and household products such as lubricants, colorants, protectants such as oils and waxes, adhesives, preservatives, and the like, as well as food-oriented applications such as condiments (mustard, ketchup, etc.).

Multiple substances may also be employed which are not only protected from inadvertent contact but segregated from one another initially (on the same face of, or on opposing faces of, the sheet material) and be commingled during the activation process or during subsequent dispensing and/or dispersion operations. Such an arrangement may be particularly useful for substances which beneficially interact with one another (e.g., co-dispensing epoxies, catalyzed reactions, etc.) to provide additional functionality with each other and/or with the target surface.

Figure 5:
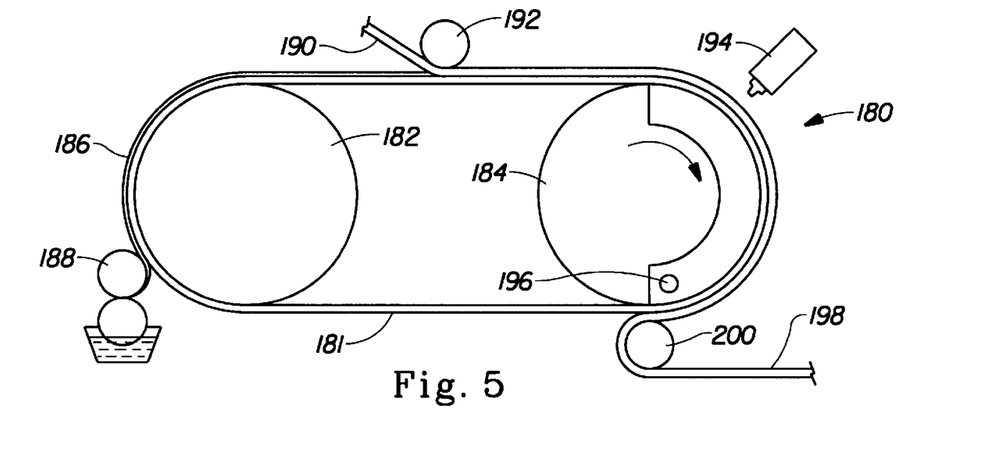
FIG. 5 is a schematic view of a suitable method for making a material of the present invention, showing a forming screen as a belt wrapped around a vacuum drum and a drive pulley.

FIG. 5 shows a suitable method for making a material such as the material 30 useful in accordance with the present invention, which is generally indicated as 180 in FIG. 5.

The first step comprises coating a forming screen with a first substance. The forming screen has a top surface and a plurality of recesses therein. The coating step applies the first substance to the top surface without bridging the recesses. A second step includes introducing a piece of material, which has a first side and a second side, onto the forming screen such that the first side is in contact with the first substance on the top surface of the forming screen. The first substance preferentially adheres to the first side of the piece of material. A third step includes forming the piece of material to create a plurality of hollow protrusions extending from the first side into the recesses of the forming screen. The plurality of hollow protrusions are spaced apart by valleys into which the first substance is transferred from the forming screen. The plurality of hollow protrusions are accurately registered with the first substance by use of a common transfer and forming surface. The first substance forms an interconnected layer in the valleys between the protrusions.

Forming screen 181 is threaded over idler pulley 182 and a driven vacuum roll 184. Forming screen 181 is preferably a stainless steel belt, having the desired protrusion pattern etched as recesses in the belt. Covering the outer surface of vacuum roll 184 is a seamless nickel screen which serves as a porous backing surface for forming screen 181.

For producing a substance containing material, a substance 186 is coated onto forming screen 181 by a substance applicator 188 while forming screen 181 rotates past the applicator. A web of material 190 is brought into contact with the substance coated forming screen at material infeed idler roll 192. Hot air is directed radially at material 190 by a hot air source 194 as the material passes over vacuum roll 184 and as vacuum is applied to forming screen 181 through vacuum roll 184 via fixed vacuum manifold 196 from a vacuum source (not shown). A vacuum is applied as the material is heated by hot air source 194. Polymer films are most easily thermoformed, whereas other materials such as foils or papers may best be embossed or hydraulically formed, wherein heating the material prior to forming may not be advantageous. A formed, substance coated material 198 is stripped from forming screen 181 at stripping roll 200. Because the same common forming screen is used to transfer the substance to the material as is used to form the protrusions, the substance pattern is conveniently registered with the protrusions.

Stainless steel forming screen 181 is a fabricated, seamed belt. It is fabricated in several steps. The recess pattern is developed by computer program and printed onto a transparency to provide a photomask for photoetching. The photomask is used to create etched and non-etched areas. The etched material is typically stainless steel, but it may also be brass, aluminum, copper, magnesium, and other materials including alloys. Additionally, the recess pattern may be etched into photosensitive polymers instead of metals. Suitable forming structures are described in greater detail in the above-referenced and above-incorporated Hamilton et al. and McGuire et al. patent applications.

The outer surface of the forming structure is treated to have a low critical surface tension so that substance 186 will not strongly adhere to it upon cooling or drying. In a preferred embodiment, the outer surface is coated with a Series 21000 proprietary release coating made by and applied by Plasma Coatings of TN, Inc., located in Memphis, Tenn. It is believed that this coating is primarily an organo-silicone epoxy. As applied to a stainless steel forming screen used in the method of the present invention, this coating provides a critical surface tension of 18 dynes/cm. Other materials which may prove suitable for providing reduced critical surface tension include paraffins, silicones, PTFE's and the like.

Figure 6:
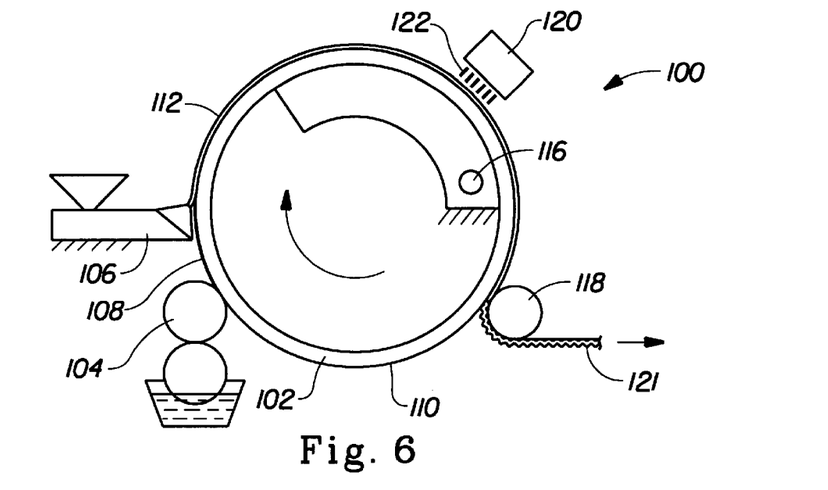
FIG. 6 is a schematic view of another suitable method for making the material of the present invention, similar to the method shown in FIG. 5, except that a film is extruded directly onto the forming drum, and an ink jet device (plurality of pressurized nozzles) injects discrete portions of substance into depressions of the hollow protrusions from outside the drum.

Material web 190 is preferably attracted to layer of substance 186, at least sufficiently so that the substance has a greater affinity for material web 190 than for forming screen 181. For example, if material web 190 is a polyolefin film, corona treating the film will improve adhesion by making the film more easily wetted. Alternatively, as shown in FIG. 6, material may be extruded directly onto the outer surface of the screen atop layer of substance 108.

Alternatives to heat and vacuum for forming protrusions in a material web are well known in the art. For example, by applying heated compressed gas to the non-substance side of the web of deformable film while the material web rests against the forming screen, protrusions may be created. Also, mechanically embossing the material web against the forming screen provides yet another forming method for use with female forming structures.

As forming screen 181 rotates, vacuum thermoforming, hydraulic forming, embossing, or combinations thereof, are completed and a formed material web 198 is thereafter discharged around a discharge idler roll 200. Automated process 180 may also have a sprayer (not shown) located upstream of substance application system 188. Such a sprayer may be used for applying a renewable release agent to the outer surface of the forming structure so that substance 186 will be preferentially attracted to material web 190. Alternatively, a permanent release agent may be applied to the outer surface to alleviate the need for such a sprayer.

Conical recesses in the forming screen may have sidewalls which have cone angles which vary from 0° to 60°. That is, the recesses may have straight sidewalls or tapered sidewalls. Straight sidewalls might be found, for example, in screens which have punched holes therein. Methods of making metal screens by photoetching are described in more detail in commonly owned U.S. Pat. No. 4,342,314 to Radel and Thompson, No. 4,508,256 to Radel et al., and No. 4,509,908 to Mullane, Jr., which are hereby incorporated herein by reference.

Drying is achieved by application of warm air or radiant heat, for example. Some substances may not require drying, such as powders or microencapsulated liquids. Substance 186 preferably does not bridge the recesses, but instead remains only on the top surface of the forming screen between recesses. Applying a low level vacuum through the recesses during spraying of the substance onto the top surface helps to avoid substance bridging of the recesses.

Because of preferential adhesion, the substance stays attached to formed material 198. Protrusion shapes other than conical may be produced by different shaped screen recesses. Recesses may be pyramidal, hemispherical, cylindrical, polygonal, and elongated, for example; however, the conical shaped protrusion is believed to provide substantially consistent inverting and/or crushing resistance. Recesses may be formed to produce different shapes and sizes and heights of protrusions within a given pattern, but again it is generally desired that protrusions be uniform so that the deformation force is predictable and consistent.

Protrusion shape has also been found to influence the stacking of material sheets or the rolling of material webs into rolls. If the same protrusion shape repeats over and over on the same spacing, for example, adjacent material sheets in a stack and adjacent layers in a roll tend to nest together, thereby negating the benefit of standoffs in protecting the substance internal to the standoffs. For situations where nesting is an issue, non-uniformly shaped or sized or spaced protrusions may be advantageous over a regular pattern of conical protrusions. Non-uniformly shaped or sized or spaced protrusions are disclosed in the aforementioned and incorporated McGuire et al. application.

Because the same common forming screen is used to transfer the substance to the material as is used to form the protrusions, the substance pattern is conveniently registered with the protrusions. In the preferred embodiment, the top surface of the forming screen is continuous except for the recesses; thus, the substance pattern is totally interconnected in this configuration. However, if a discontinuous pattern of substance were coated onto the forming screen, a discontinuous substance pattern between protrusions would result.

It is believed that the protrusion size, shape and spacing, the web material properties such as flexural modulus, material stiffness, material thickness, hardness, deflection temperature as well as the forming process determine the strength of the protrusion. The forming process is important in polymer films for example, since "cold forming" or embossing generates residual stresses and different wall thickness distributions than that produced by thermoforming at elevated temperatures. For some applications it is desirable to provide a stiffness (deformation resistance) which is sufficient to withstand a pressure of at least 0.1 pounds per square inch (0.69 kPa) without substantially deforming protrusions to where the substance contacts an external surface. An example of this requirement would be the need to wind the web onto a roll for transport and/or dispensing. Even with very low in-wound pressures of 0.1 pounds per square inch (0.69 kPa), a residual in-wound pressure in the interior of the roll may deform protrusions in the web sufficiently to bring the overlaying web layers into contact with the substance. A "threshold" protrusion stiffness is required to prevent this winding damage from occurring. Similarly, when the web is stored or dispensed as discrete sheets, this "threshold" stiffness is required to prevent premature activation of the product due to the weight of overlaying layers of sheets or other forces, such as forces induced by shipping vibrations, mishandling, dropping and the like.

FIG. 6 depicts another method of forming a material, generally indicated as 80. Method 80 has a deformable material 82 placed onto a forming screen 84. Forming screen 84 has a top surface 86 and recesses 88. Top surface 86 is coated with a substance 90 such that substance 90 does not bridge recesses 88. Material 82 is placed on top of substance 90 as in the embodiment illustrated by FIG. 5. However, FIG. 6 shows a positive pressure forming force H applied to material 82 from above the screen instead of a vacuum force applied from below the screen. Forming force H may originate from a liquid applied under pressure against material 82, such as occurs in hydraulic forming. Forming force H may also be generated by application of a pressurized gas, perhaps heated. A preferred fluid for use in a positive pressure forming application is heated water, the use of which is described in greater detail in commonly assigned U.S. Pat. No. 4,695,422 to Curro et al., No. 4,778,644 to Curro et al., and No. 4,839,216 to Curro et al., which are hereby incorporated herein by reference.

FIG. 6 discloses an alternative process generally indicated as 100. Process 100 has forming screen 102, which is curved to form a drum. A substance source and application system 104 are positioned upstream of an extruder 106. Substance application system 104 deposits a thin coating of a substance 108 onto an outer surface 110 of forming screen 102. Outer surface 110 is treated to have a low critical surface tension so that substance 108 will preferentially adhere to a material introduced onto substance 108 rather than to outer surface 110 when substance 108 is dried or cooled. Process 100 is different from process 30 in that a material 112 is created by directly extruding material 112 onto forming screen 102 instead of metering a preformed web thereon. Material 112 is laid on top of layer of substance 108 and material 112 has a greater affinity for substance 108 than does outer surface 110, so that substance 108 is effectively transferred to material 112 when contact between them occurs.

As forming screen 102 rotates past extruder 106, material 112 is formed as shown in FIG. 5. A vacuum manifold 116 is illustrated with forming screen 102 so as to draw material 112 around layer of substance 108 and into recesses in forming screen 102 for forming hollow protrusions. Once formed, hollow protrusions preferably pass under an "ink jet" type substance injection delivery system 120 (pressurized nozzle array comprising a plurality of pressurized nozzles), which deposits a spot of substance 122 into the depression of each hollow protrusion from outside forming screen 102, resulting in a formed material 121. Although registration is required between substance injection system 120 and the hollow protrusions, system 120 may be registered directly from the recesses in forming screen 102, which define the location of the protrusions. This is much less difficult than would be registration with a transient web of material, particularly very thin webs. Formed material 121 is thereafter discharged around a discharge idler roll 118.

Figure 7:
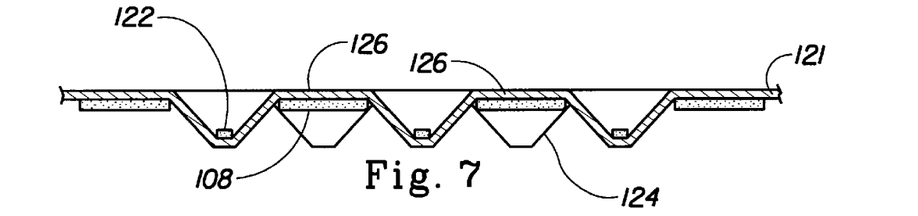
FIG. 7 is an elevational sectional view of the material according to the present invention resulting from the method of FIG. 6, showing the substance portions attached to both sides of the formed material, both substances being protected by the same standoff protrusions.
Figure 8:
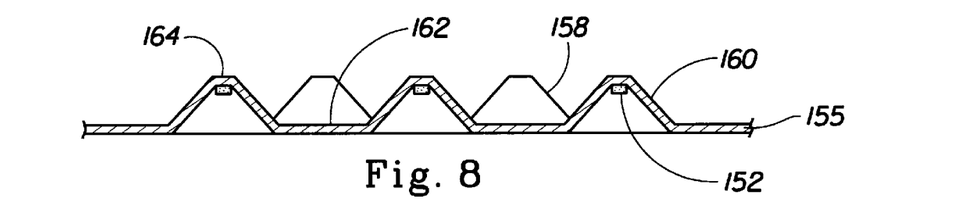
FIG. 8 is an elevational sectional view of another material according to the present invention which may be obtained from the method of FIG. 6.

FIG. 7 shows formed material 121 after it leaves process 100. Formed material 121 has protrusions 124 and valleys 126 surrounding protrusions 124. Located in valleys 126 is preferably an interconnected, continuous layer of substance 108. Although, as described earlier, a discontinuous application of substance to the forming screen results in a discontinuous pattern of substance on material 121. Inside depressions of hollow protrusions 124 are discrete spots of substance 122. Substance 108 and substance 122 may be the same, such as a pressure sensitive adhesive. If a pressure sensitive adhesive, substances 108 and 122 are on opposite sides of formed material 121, protected from contact with external surfaces adjacent to material 121 by being located in two different types of protected locations, namely both the valleys and inside the hollow protrusions. In this situation, the formed material together with adhesive 108 and 122 may function as a double-sided tape. Substances 108 and 122 could be distinctly different from each other and serve different purposes, however. Alternatively, as shown in FIG. 8 a similar material 155 could be produced having the substance 152 located only within the conical protrusions 158.

Other manufacturing processes could be utilized, including those in which a male-type forming structure replaces the female-type forming structures depicted in FIGS. 5 and 6 with their accompanying recesses. Such alternative processes include those described in greater detail in the above-referenced and incorporated U.S. patent application Ser. No. 08/744,850, filed Nov. 8, 1996 in the names of Hamilton and McGuire entitled "Material Having A Substance Protected by Deformable Standoffs and Method of Making".

Any other suitable method of manufacture which delivers satisfactory results for the given substance and sheet material utilized may be employed, including but not limited to manual methods of uniting the substance and sheet material. One such alternative would be a method similar to that of FIG. 6, but wherein the incoming sheet of material is already pre-existing as a web of material rather than being extruded onto the forming screen 84. Another adaptation of the method of FIG. 6 would employ a doctor blade or squeegee assembly which would replace the pressurized nozzle delivery system 120 to meter the substance into the depressions corresponding to the hollow protrusions and ensure that the substance in the finished sheet material is in the protected location below the outermost surfaces of the sheet material.

Figures 9, 10:
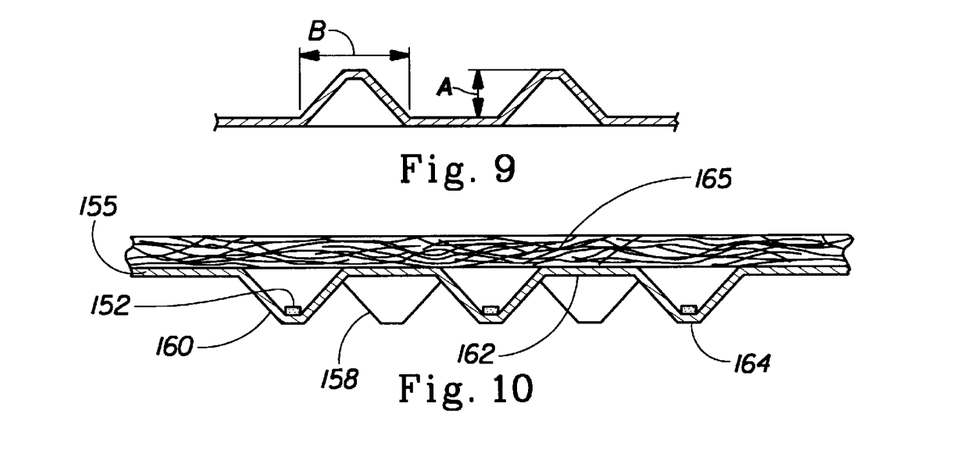
FIG. 9 is an elevational sectional view of the material formed by the method of FIG. 5 or by the method of FIG. 6, showing preferred dimensional relationships of protrusions.
FIG. 10 is another embodiment of a material in accordance with the present invention, including a porous material spanning the protected substance.

FIG. 9 shows a preferred shape of the protrusions and valleys of the present invention, which enables protrusions to substantially invert and/or crush as a mode of deforming. The preferred shape minimizes protrusion fold-over and interference with substance placed in valleys between protrusions, or inside hollow protrusions, or both. Also, the preferred shape helps to ensure a repeatable, predictable, resistance to protrusion deformation. FIG. 9 shows that each protrusion is defined by a height dimension A and a base diameter dimension B. A preferred ratio of base diameter B to height A, which enables protrusions to substantially invert and/or crush without fold-over, is at least 2:1.

Deformation mode and force can be influenced by the sidewall thickness profile to provide more desired results. A protrusion's sidewall connects the outermost portion of the protrusion to the unformed material adjacent to base perimeter of the protrusion. The sidewall as defined may also contain a peripheral region substantially within the outermost portion which is substantially thinner than the interior region of the outermost portion. Protrusions where at least a portion of the sidewalls are substantially thinner than the unformed material adjacent to the base perimeter are believed preferred for deformation by the user. Sidewalls that are also substantially thinner in at least a portion of the sidewall as compared to the material at the outermost portion of the protrusion also beneficially bias the deformation to occur primarily within the sidewall structure.

In structures containing relatively small protrusions, as found in high number density protrusion patterns, such thinner sidewall gauges can be particularly useful.

Methods of production can influence the sidewall thickness profile such as in the use of a forming screen with essentially straight screen walls which define the forming screen hole. Such a process allows for substantially thinner sidewall thickness since the protrusion is freely drawn from the base perimeter into the forming screen recess to the point of contact with the internal backup screen. The internal backup screen's purpose is to prevent further drawing of the protrusion. This approach yields a more varied gauge profile within the sidewalls.

Micro-texturing the material during forming may also be useful, such as in producing a distinction between one side of the material and the other side. Micro-texturing of the outermost surface features of the three dimensional structure may be achieved in the present invention, for example, by drawing the piece of material into forming screen recesses and against a micro-textured surface, such as a vacuum drum having tiny apertures therein.

FIG. 10 depicts another embodiment of a material in accordance with the present invention, structurally similar to that depicted in FIG. 8. However, in addition to the structural elements of FIG. 8 the material of FIG. 10 includes an additional structural element in the form of one or more layers of a porous material 165 which overlies the protected substance 152 from the side opposite to that protected by the sheet material. Porous material 165 may be any material sufficiently porous as to not block or significantly impair the ability of the substance 152 to be dispensed from the sheet material onto the target surface, against which the porous material would be placed. Porous materials may comprise, as depicted in FIG. 10, a fibrous material such as a woven or nonwoven material, a scrim or mesh-like material, a porous or apertured film or the like, of similar or diverse composition to that of the sheet material itself. Any of the aforementioned types of sheet-like materials may be utilized. The inclusion of such a porous material provides additional protection for the substance prior to activation of the sheet material and may provide additional distributive benefit to more evenly disperse the substance onto the target surface particularly when translational motion of the sheet material is also employed. The porous material may also provide additional interaction with the substance such as for shear-thinning substances and may provide additional benefits such as lathering or foam generation, etc. One application envisioned for such a structure would be a cleansing cloth which provides its own source of cleansing agent.

In general, the present invention is a three dimensional structure for holding a substance protected from inadvertent contact with external surfaces. The structure is convertible to a substantially two dimensional structure by applying a compressive force so that the structure collapses to release or expose the substance into contact with external surface(s). However, the scope of the invention also applies to three dimensional structures holding substances from inadvertent contact, which are converted to substantially two dimensional structures by means other than compression. For example, the inventors have found that a tensile force applied to the same three dimensional structure can cause it to plastically deform longitudinally and thereby contract in caliper or thickness to similarly expose or release substance. It is believed that under sufficient tension, the material between protrusions deforms in response to forces in the plane of the material and that protrusions are thereby elongated in the same direction. When the protrusions are elongated, they are reduced in height. With enough elongation the protrusions are reduced in height to where the substances between them, in them, or both are exposed.

A combination of compression and tensile forces may be applied to the material of the present invention in order to expose a substance from within the three dimensional structure. Although in a preferred embodiment of the present invention, the tensile force necessary to achieve sufficient deformation of said three dimensional structure in order to expose substance to an external surface is significantly greater than a compressive force to achieve the same result, a structure may be designed which is more easily deformed by a tensile force applied in a specific planar direction. For example, a structure may have parallel waves instead of protrusions and the waves may be easily flattened by stretching the structure perpendicular to the waves but in the plane of the waves. Other suitable tensile response structures are disclosed in U.S. Pat. No. 5,518,801 to Chappell et al. which is hereby incorporated herein by reference.

In another example, heat could be applied to cause the same structure made of shrinkable film to reduce in thickness to similarly release or expose the substance.

Examples of uses of the three dimensional structure of the present invention besides tapes, labels, and storage wraps include: lotion impregnated facial tissues, scented strips containing microencapsulated perfumes, adhesive impregnated shelf and wall paper, medicinal patches, patterned condiment delivery to a surface, two component adhesives, laundry pre-treating chemicals, abrasive delivery systems, and other applications where avoidance of contact with a substance held in a substrate is desired until some action is taken.

As described hereinafter, different substances can be deposited on the opposing faces of the formed material. Multiple substances can be located on the same face of the material either geometrically spaced from each other or commingled. Substances can be partially layered. An example is a layer of adhesive adjacent to the material surface with a solid particulate adhered to the exposed side of the adhesive layer. As discussed previously, multiple substances which are initially separated (on the same face of, or on opposing faces of, the sheet material) may be commingled during the activation process or during subsequent dispensing and/or dispersion operations.

A pattern of protrusions can be superimposed either on a similar dimensional scale or on a different dimensional scale such as a single or multiple "microprotrusion" pattern located on the tops of other larger protrusions.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A substance delivery system comprising:
   (a) a three-dimensional structure having outermost surface features and spaces between said outermost surface features for containing a substance, said substance having a level internal to said outermost surface features such that said substance is protected from inadvertent contact with external surfaces; and
   (b) a substance, having substantial resistance to flow prior to delivery to a target surface, occupying said spaces of said three-dimensional structure, said substance remaining protected until said three dimensional structure is sufficiently deformed into a substantially two dimensional structure and said substance is thereby exposed to contact an external surface without compliance of said external surface being necessary, said substance having an effective viscosity upon activation which permits said substance to be liberated from said location and dispensed onto said target surface.

2. The substance delivery system of claim 1, wherein said spaces are interconnected.

3. The substance delivery system of claim 1, wherein said substance exhibits a greater flowability after said three-dimensional structure is deformed.

4. The substance delivery system of claim 3, wherein said substance comprises a shear-thinning substance.

5. The substance delivery system of claim 1, wherein said spaces are discrete.

6. The substance delivery system of claim 1, wherein said three-dimensional structure is deformable by a compression force applied substantially perpendicular to a plane defined by said three-dimensional structure and wherein said outermost surface features of said three-dimensional structure deform in a direction substantially perpendicular to said plane.

7. The substance delivery system of claim 1, wherein said three-dimensional structure is deformable by a tensile force applied substantially parallel to a plane defined by said three-dimensional structure and wherein said outermost surface features of said three-dimensional structure deform in a direction substantially perpendicular to said plane.

8. The substance delivery system of claim 1, wherein said substance delivery system further comprises a sheet of porous material such that said substance is located between said three-dimensional structure and said sheet of porous material and may be dispensed through said sheet of porous material.

9. The substance delivery system of claim 8, wherein said sheet comprises a fibrous material.

10. The substance delivery system of claim 1, wherein said substance is selected from the group consisting of cleansing agents, medicinal agents, emollients, lubricants, colorants, preservatives, protectants, condiments, adhesives, fragrances, anti-perspirants, deodorants, and combinations thereof.

11. The substance delivery system of claim 1, wherein said substance delivery system includes at least two substances of diverse composition.

12. A selectively-activatible sheet material for dispensing and dispersing a substance onto a target surface, said sheet material comprising:

(a) a three-dimensional sheet of material having a first side and a second side, said first side having a plurality of hollow protrusions extending outwardly therefrom and separated from one another by valleys, said second side having a plurality of depressions corresponding with said plurality of hollow protrusions; and (b) a substance adhering to and partially filling a location protected from external contact comprising at least one of said valleys and said depressions, such that said sheet material may be selectively activated by deforming said hollow protrusions to deliver said substance to a target surface, said substance having an effective viscosity upon activation which permits said substance to be liberated from said location and dispensed onto said target surface.

13. The selectively-activatible sheet material of claim 12, wherein said substance adheres to and partially fills said depressions.

14. The selectively-activatible sheet material of claim 12, wherein said substance adheres to and partially fills said valleys.

15. The selectively-activatible sheet material of claim 12, wherein said substance is selected from the group consisting of cleansing agents, medicinal agents, emollients, lubricants, colorants, preservatives, protectants, condiments, adhesives, fragrances, antiperspirants, deodorants, and combinations thereof.

16. The selectively-activatible sheet material of claim 12, wherein said sheet material includes at least two substances of diverse composition.

17. The selectively-activatible sheet material of claim 12, wherein said substance exhibits a greater flowability after said sheet material is activated.

18. The selectively-activatible sheet material of claim 12, wherein said hollow protrusions are deformable by a compression force applied substantially perpendicular to a plane defined by said three-dimensional sheet of material and wherein said hollow protrusions deform in a direction substantially perpendicular to said plane.

19. The selectively-activatible sheet material of claim 12, wherein said hollow protrusions are deformable by a compression force applied substantially parallel to a plane defined by said three-dimensional sheet of material and wherein said hollow protrusions deform in a direction substantially perpendicular to said plane.

20. A selectively-activatible sheet material for dispensing and dispersing a substance onto a target surface, said sheet material comprising:

(a) a three-dimensional sheet of material having a first side and a second side, said first side having a plurality of hollow protrusions extending outwardly therefrom and separated from one another by valleys, said second side having a plurality of depressions corresponding with said plurality of hollow protrusions;

(b) a substance adhering to and partially filling a location protected from external contact comprising at least one of said valleys and said depressions, such that said sheet material may be selectively activated by deforming said hollow protrusions to deliver said substance to a target surface, said substance having an effective viscosity upon activation which permits said substance to be liberated from said location and dispensed onto said target surface; and (c) a sheet of porous material at least partially joined to said three-dimensional sheet of material such that said substance is located between said three-dimensional sheet of material and said sheet of porous material and may be dispensed through said sheet of porous material.

* * * * *